United States Patent [19]

Meruelo et al.

[11] Patent Number: 5,326,788

[45] Date of Patent: * Jul. 5, 1994

[54] BIOLOGICAL FLUID PURIFICATION SYSTEM

[75] Inventors: Daniel Meruelo, Scarborough; Gad Lavie, New York, both of N.Y.

[73] Assignee: New York University, New York, N.Y.

[*] Notice: The portion of the term of this patent subsequent to Sep. 22, 2009 has been disclaimed.

[21] Appl. No.: 907,080

[22] Filed: Jul. 1, 1992

Related U.S. Application Data

[63] Continuation of Ser. No. 299,971, Jan. 19, 1989, Pat. No. 5,149,718.

[51] Int. Cl.$^5$ .................. A61K 31/05; A61K 31/045; A61F 5/44; A61B 19/00
[52] U.S. Cl. .................... 514/732; 514/738; 604/347; 604/349; 604/403; 604/408; 604/416; 435/2; 424/DIG. 14
[58] Field of Search ............... 514/732, 738, 764, 762; 604/349, 347, 403, 408, 416; 435/2; 424/DIG. 14

[56] References Cited

U.S. PATENT DOCUMENTS

| | | | |
|---|---|---|---|
| 2,707,704 | 5/1955 | Brockmann et al. | 204/157.91 |
| 4,405,323 | 9/1983 | Auerbach | 604/285 |
| 4,755,170 | 7/1988 | Golden | 604/52 |
| 4,855,064 | 8/1989 | Schlein | 210/764 |
| 4,872,464 | 10/1989 | Loeb et al. | 128/844 |
| 4,898,891 | 2/1990 | Lavie et al. | 514/732 |
| 5,149,718 | 9/1992 | Meruelo et al. | 514/732 |

FOREIGN PATENT DOCUMENTS 59-304493 10/1984 Japan .

OTHER PUBLICATIONS

Halm, Ivan, *Gyogyszereszet* 23:217-218 (1973).
Sedariston Product Information. Steiner Arzneinittel Ostpreubendamm. 72-74, 1000 Berlin.
Brockmann, H. H., *Progress in Organic Chemistry I*, Cook, J. W. ed., pp. 64-82, Academic Press, N.Y. (1952).
Banks, J. H. et al., *Aust. J. Chem.* 29:1502-1521 (1976).
Roderwald, G. et al., *Angew. Chem. Int. Ed. Eng.* 89: 56 (1977).
Adamski, R. et al., *Chem. Abs.* 75:183 (1971).
Weiss, U. et al., *Progress in Organic Chemistry* 52:1-71 (1987).
Muldner, H. et al., *Arzneim—Forsch.* 34:918 (1984).
Okpanyi, S. N. et al., *Arzneim—Forsch.* 37:10 (1987).
Brockmann, H. et al., *Tetrahedron Letters* 23:1991-1994 (1974).
Daniek, K., *Hippokrates* 19:526 (1949) (*Chemical Abstract* 46:9721e (1952)).
Song, P-S. et al., *Biophys. J.* 35:551-555 (1981).
Derbentseva, N. A., *Chem. Abstr.* 78:67530 (1973).
Mishenkov, E. L., et al., *Chem. Abstr.* 85:187161Y (1976).
Brockmann, H. et al., *Chem. Ber.* 90:2480 (1957) (*Chem. Abstr.* 52:163 (1958)).
Brockmann, H. et al., *Chem. Ber.* 90:2302 (1957).
Brockmann, H. et al., *Tetrahedron Letters* 1:37-40 (1975).
Meruelo, D. et al., *Proc. Natl. Sci. USA* 85:5230-5234 (1988).
Ahmed, S. A. et al., *J. Chem. Soc. Commun.* 883-884 (1987).
Spitzner, D., *Angew Chem. Intl. Ed. Eng.* 89:55 (1977).
Neumann, H. *Chem. Abstract* 66:8300 (1967).
Knox et al., "Isolation and activity of the photodynamic pigment hypericin," *Plant, Cell and Environment* 8:19-25 (1985).

*Primary Examiner*—Nathan M. Nutter
*Attorney, Agent, or Firm*—Browdy & Neimark

[57] ABSTRACT

The present invention provides compositions, articles and methods for inactivating viruses present in whole blood and other body fluids. The method comprises contacting the body fluids with an effective amount of an antiviral compound. Blood bags, vacuum blood tubes, condoms, spermicidal jellies and vaginal lubricants containing effective amounts of the antiviral compounds are also provided.

31 Claims, 3 Drawing Sheets

BIOLOGICAL FLUID PURIFICATION SYSTEM

This is a continuation of application Ser. No. 07/299,971, filed Jan. 19, 1989 and now U.S. Pat. No. 5,149,718.

BACKGROUND OF THE INVENTION

This invention relates to compositions and methods for inactivating viruses and retroviruses present in blood, other body fluids and, more generally, biological fluids, and to articles used in the practice of such methods.

Human Immunodeficiency Virus (HIV), the causative agent of AIDS, is currently being spread in epidemic proportions in susceptible populations around the world. Two different serotypes of the virus, designated HIV-1 and HIV-2, have been identified. In patients infected with HIV, contaminating virus can frequently be cultivated from body fluids including blood, urine, cerebrospinal fluid, tears, semen and salivary secretions. The presence of virus in these fluids constitutes a health risk not only for uninfected individuals who are exposed to them, but especially for health care workers who must treat infected patients.

Transmission of HIV infection to transfusion recipients by vitally contaminated blood and/or blood products has been well-documented. Over one thousand cases of HIV infection acquired via blood transfusion have been reported in the United States. In addition, it is estimated that an additional 12,000 individuals may have acquired the virus by this route between 1978 and 1984 before routine screening for HIV was instituted in blood banks. It is estimated that 90–100% of recipients of such HIV-contaminated transfusions become infected. Although routine serological testing of donated blood began in 1985, a significant risk of HIV infection for blood transfusion recipients still exists because of limitations in the HIV-screening procedures. Current testing procedures (which involve screening for antibodies to HIV) may fail to identify HIV-infected blood donors for at least six months post infection and chronic carriers of HIV sometimes test negative even in the presence of progressive HIV infection.

Moreover, health care workers who become infected by blood-borne virus by accidental needle sticks and blood spills constitute another risk group that is independent of the screening procedures and their limitations.

Another risk group includes sex partners of HIV-infected individuals. Transmission of HIV infection by virally contaminated semen apparently accounts for the spread of HIV by sexual contact. Although transmission of infection by virally contaminated urine, cerebrospinal fluid, tears or saliva has not been reported, risk of such transmission is present nonetheless.

Numerous chemical and physical methods have been used in an effort to inactivate HIV present in biological fluids or in the laboratory equipment used to analyze such fluids. Exposure to alcohols such as ethanol or isopropanol, paraformaldehyde, buffered formalin, hydrogen peroxide, hypochlorite, detergents such as NP-40, heat, high and low pH, as well as commercial disinfectants (such as LYSOL®) are the most widely employed techniques for inactivating HIV. These agents show varying degrees of effectiveness in inhibiting the viral reverse transcriptase activity of HIV or otherwise reducing the number of infectious HIV particles. However, virtually all of these techniques would interfere with the known clinical tests for detection of HIV, particularly those tests that are dependent on maintaining the viability of cells or infectious agents (other than HIV) that are present in the sample to be tested. A further drawback is that these agents are not appropriate for use in blood or blood products intended for transfusion. Also, use of the known agents by health care workers involved in handling blood or other body fluids, or in transfusing potentially infected blood or blood products, is often impractical.

The use of Nonoxynol-9 (nonylphenoxypolyethoxyethanol, a spermicidal polyethoxylated phenol) and other spermicidally active compounds as a lubricant or coating in condoms and other contraceptive articles and preparations has been reported to inactivate HIV. Nonoxynol-9 has been reported to be effective against free virus at concentrations in excess of 0.05% (vol/vol). However, Nonoxynol-9 may not inactivate the virus when it is present within HIV-infected cells, a source of infectious HIV.

Accordingly, what is needed in the art is a method for treating biological fluids in order to inactivate viral particles and in particular retroviruses such as HIV which may be present in these fluids, before the contaminated fluid causes an individual to become infected.

Therefore, it is the object of the present invention to provide a method, articles and compositions for inactivating viruses and especially retroviruses that may be present in body fluids.

Another object of the present invention is to provide a method, articles and compositions for inactivating HIV and other viruses and retroviruses present in whole blood and in other body fluids.

These and other objects of the present invention will be apparent to those of ordinary skill in the art in view of the present description, appended claims and accompanying drawings.

SUMMARY OF THE INVENTION

One aspect of this invention relates to an article of manufacture comprising means for retaining a biological fluid and an effective antiviral (and/or anti-retroviral) amount of at least one antiviral compound selected from the group consisting of antiviral aromatic polycyclic diones, isomers, homologs, analogs, derivatives and salts of said diones and mixtures thereof, said amount being in antiviral (and/or anti-retroviral) association with said fluid when said fluid is in said retaining means.

Another aspect of this invention relates to a method for reducing or abolishing the infectivity of viruses and/or retroviruses present in a biological fluid by contacting said fluid with an antiviral (and/or anti-retroviral) effective amount of an antiviral compound.

DETAILED DESCRIPTION OF THE INVENTION

All patent applications, patents and literature references referred to in this specification are hereby incorporated by reference in their entirety.

The present invention is based on the unexpected finding that certain antiviral compounds can be used to substantially reduce or completely abolish the infectivity of viruses and retroviruses, and HIV in particular, that may be present in samples of biological fluids. This termination or reduction in infectivity is accomplished without causing significant interference with most of the routine clinical laboratory tests performed on such samples. The antiviral agents employed to inactivate the virus or retrovirus accomplish this function without rendering blood or blood products toxic or otherwise useless for transfusion or administration to mammals. It is anticipated that the antiviral compounds of the invention will not interfere with the performance of ELISA (enzyme linked immunosorbent assay) and Western blot assays used to detect antibodies to HIV present in biological fluids such as urine and serum. This is based on the fact that the antiviral compounds of the invention do not appear to have any significant effect on the usual constituents of mammalian blood or on blood chemistry as determined by clinical testing (see Example 2, below). There is no reason to believe that the presence of the antiviral compounds of the present invention will affect the structural or mechanical properties (e.g. tensile strength) of the materials (e.g. glass, plastic, etc.) used in the construction of containers and devices employed for holding, handling, storing or processing biological fluids or cause any other adverse activity (e.g. reactivity with the biological fluid or container, etc.).

As used herein inactivation of a virus (or retrovirus) refers to substantially reducing or eliminating the ability of the virus to infect mammalian cells. Such inactivation refers to free virions as well as viral budding and propagation of infection by cell fusion. Thus, an effective amount for inactivating a virus (or retrovirus) of the antiviral compounds of the present invention is an amount that will eliminate the ability of a virus (or retrovirus) to infect and/or invade mammalian cells.

The antiviral compounds of the invention may be incorporated into (or used to clean and disinfect) articles such as containers, receptacles, vacuum bags, blood bags, syringes, needles, tubing and other medical or laboratory devices and equipment used for the collection, retention, storage, processing, handling or testing of biological fluids. The antiviral compounds of the invention may also be employed to inactivate HIV, and other retroviruses (as well as viruses) in human blood products used for transfusion by incorporating the compounds directly into articles and devices, such as flexible plastic bags, used to store and transfuse blood. In another application the antiviral compounds of the invention are used with male and female contraceptive devices and compositions to inactivate HIV and other retroviruses and viruses present in semen or vaginal fluid, thus inhibiting sexual transmission of infections due to such viruses.

The antiviral compounds have a wide-spectrum of effectiveness in inactivating viruses and retroviruses, and are especially effective in the inactivation of enveloped viruses. Non-limiting examples of the virus whose infectivity can be inhibited through exposure to the antiviral compounds of the invention are HTLV-I, HTLV-II, HTLV-III (also known as HIV), hepatitis-B virus, cytomegalovirus, Herpes Simplex Virus, etc. Also inactivated by exposure to the antiviral compounds are the viruses responsible for animal diseases, such as sheep lentiviruses (e.g. caprine arthritis encephalitis virus, Visna virus, bovine leukemia virus, vesicular stomatitis virus (VSV), etc.).

"Biological fluids" are defined herein to include blood, serum, blood products (such as plasma, platelet concentrates, erythrocytes, cyroprecipitates, immunoglobulin concentrates, clotting factor concentrates, e.g., antihemophilic factor or von Willenbrand factor), semen, cerebrospinal fluid, mucus, vaginal fluids, tears, feces, urine, sweat, saliva, culture media, buffer solutions, laboratory reagents and processing solutions, etc.

"Antiviral compounds" includes aromatic polycyclic dione compounds (such as hypericin, pseudohypericin, etc.), as well as physiologically acceptable isomers, homologs, analogs, derivatives and mixtures thereof having antiviral and/or anti-retroviral activity in that they abolish or reduce the infectivity of viruses and retroviruses.

For purposes of the preceding definition of Antiviral Compounds, "homologs" shall mean compounds with structural formulas that differ from the aromatic polycyclic diones of the present invention by one or more carbon atoms and one or more hydrogen atoms or pairs of hydrogen atoms (see by way of non-limiting example compounds XVI and XVII below; see also the upper left-hand corner compound in the table of compounds synthesized according to U.S. Pat. No. 2,707,704 and its homologs wherein one or more of the R groups have been replaced by ethyl and/or hydrogen and compounds 8 and 10 disclosed in Banks, H. J. et al., infra etc.). "Isomers" shall mean compounds having the same molecular formula as the polycyclic aromatic diones of the present invention and shall include, without limitation, structural isomers, enantiomers, position isomers, optical isomers and stereoisomers (e.g. cis and trans, + and −, d and l) (see, by way of non-limiting example, compound 17 of Banks et al. infra and its isomer wherein, e.g. the hydrogen atoms in the center would be oriented both below or above the plane of the paper and compound 25 of Weiss, U. et al., infra which has several asymmetric carbon atoms and its various optical isomers). "Analogs" shall include polycyclic aromatic compounds having the same ability as the present diones (e.g., compounds 13, 21, 22 in Weiss, U. et al. infra). "Derivatives" shall include compounds bearing a strong structural similarity to the present diones but having one or more substitute groups in or more positions (see, e.g. compounds 7 and 9 of Banks; benzoic acid derivatives of the upper left compound of Brockmann, et al., infra and hydroxylated, esterified, alkyl-substituted and otherwise substituted derivatives of the compounds specifically disclosed herein). A non-limiting list of antiviral compounds is set forth on Appendix A.

Salts of these Antiviral Compounds which are soluble in aqueous media and physiologically acceptable are particularly preferred. "Salts" shall mean both complex salts (such as compound 25) and ionic salts.

"Biological fluid retaining articles" are defined herein in a non-limiting fashion to include blood bags, vacuum blood tubes, test tubes, laboratory glassware, urine cups, condoms and other devices and articles used for the collection, retention, storage or processing of biological fluids.

"Retroviruses" are defined herein as viruses containing an RNA genome and an RNA-dependent DNA polymerase (reverse transcriptase) enzymatic activity. All retroviruses have common morphological, biochemical and physical properties that justify their inclusion into a single virus family. These parameters are summarized in Table 1 below, RNA Tumor Viruses, Weiss, R. et al. eds., Cold Spring Harbor Press, New York,

TABLE 1
GENERAL PHYSICAL PROPERTIES OF KNOWN RETROVIRUSES

| | |
|---|---|
| Nucleic acid | linear positive-sense single-stranded RNA (60S-70S) composed of identical subunits (30S-35S); 5' structure ($m^7G^5ppp^5NmpNp$); polyadenylated 3' end; repeated sequences at 3' and 5' ends; tRNA base-paired to genome complex |
| Protein | above 60% by weight; gag, internal structural proteins; pol, reverse transcriptase; env, envelope proteins |
| Lipid | about 35% by weight; derived from cell membrane |
| Carbohydrate | about 4% by weight; associated with envelope proteins |
| Physiochemical properties | density 1.16–1.18 g/ml in sucrose, 1.16–1.21 g/ml in cesium chloride; sensitive to lipid solvents, detergents, and heat inactivation (56° C., 30 min); highly resistant to UV- and X-irradiation |
| Morphology | spherical enveloped virions (80–120-nm diameter), variable surface projections (8-nm diameter), icosahedral capsid containing a ribonucleoprotein complex with a core shell (nucleoid) |

In addition to the above retrovirus properties, the genome of HIV encodes at least five other proteins, designated TAT, ART/TRS, 3'-ORF, SOR and R whereas HTLV I contains the pX gene which may encode up to four proteins. (Seiki et al. Science 228: 1532–1534, 1985.).

All retroviruses have similar overall chemical composition. In general, they comprise about 60–70% protein, 30–40% lipid, 2–4% carbohydrate, and about 1% RNA. The envelope of retroviral particles is derived from the cell-surface membrane, and most, if not all, of the lipids in viral particles are located in the unit-membrane envelope of the virion. Non-limiting examples of retroviruses include Friend Leukemia Virus (FV), Radiation Leukemia Virus (RadLV), Feline Leukemia Virus, Avain Myeoblastosis Virus, and the human T-cell lymphotropic virus family (HTLV I, II, III and IV; HTLV III is also known as Human Immunodeficiency Virus or HIV). HTLV I has been shown to cause adult T cell leukemia and HTLV II hairy cell leukemia. HTLV IV is related to simian immunodeficiency virus and has been found in African natives suffering from AIDS; its relationship to HTLV III is currently under investigation. In this specification, It "viral" or "virus" will be understood to include "retroviral" or "retrovirus" respectively unless the context requires otherwise.

The antiviral compounds of the present invention are capable of inactivating HIV (i.e. abolishing or substantially reducing the infectivity of free virions as well as preventing virus budding from infected cells and inhibiting propagation of infection via cell fusion, i.e. fusion between HIV-infected lymphocytes and uninfected lymphocytes which takes place even in the absence of free virus) related retroviruses and other viruses in whole blood and other bodily fluids. These compounds have been found to display effective viral inactivating properties when the compounds are in direct contact with the virus to be inactivated. This is in contrast to other known antiviral drugs, such as azidothymidine (AZT) which are only effective in inhibiting intracellular viral replication in intact cells. As shown below in Example 1, hypericin abolished the infectivity of HIV at concentrations as low as 0.77 micrograms/ml. Exposure to hypericin does not interfere with the performance or results of the well-known clinical laboratory tests on blood i.e. CBC, hemoglobin, SMA12, etc., and should not interfere with or complicate performance or results of the usual clinical tests carried out on urine or cerebrospinal fluid which contain some of the same or similar components. The antiviral compounds used in the present invention have low cellular toxicity and do not substantially interfere with cell viability or functions when used at concentrations effective to inhibit or terminate the infectivity of HIV or other viral species (in both in vitro and in vivo testing using mammals and mammalian—including human—cells). Accordingly, exposure to hypericin or the other antiviral compounds of the invention should not interfere with the activity or usefulness of human and animal blood products used for transfusion, such as red blood cells, platelets, fresh frozen plasma, cryoprecipitate blood factors, etc.

In addition, it is now known that a retrovirus related to HIV, HTLV-1, can be found in the blood of infected individuals. HTLV-1 has been shown to cause diseases in humans including T-cell leukemias and neurological illnesses and is common in some populations in the United States and Japan. Similar neurological diseases occur in goats (e.g caprine arthritis encephalitis caused by the homologous virus) and sheep (e.g. scrapie caused by Visna virus). Testing for HTLV-1 is not currently performed on collected blood. Due to the similarities between HIV and HTLV-1, (and the effectiveness of the aromatic polycyclic dione compounds as anti-retroviral agents) it is fully expected that the antiviral compounds used in the present invention will inactivate HTLV-1 and other retroviruses present in biological fluids, notably in human and domestic animal blood, etc. Thus, blood collected for transfusion can be made free of infectious virus at the time of collection by incorporation of an effective amount for terminating infectivity of hypericin, for example, into the container that is employed to collect the whole blood from the blood donor. As shown in Example 3 below, it is believed that exposure to hypericin will not destroy or otherwise significantly reduce the biological or therapeutic function of blood products (e.g. platelets, red blood cells, immunoglobulin concentrates, antihemophilic factor, etc.). In addition, based on previous experiments with the in vivo administration of hypericin to mice, as disclosed in copending U.S. patent applications Ser. No. 084,008 of Lavie et al. filed Aug. 10, 1987 and Ser. No. 172,064 of Meruelo et al. filed Mar. 23, 1988, collected blood containing one or more of the antiviral compounds of the present invention in sufficient concentrations to significantly reduce or terminate the infectivity of HIV or other virus, should be non-toxic when reinfused into transfusion recipients.

HIV isolated from the blood of an AIDS patient and cultured on H9 cells was completely inactivated by exposure to 2.5 micrograms/ml of hypericin for one hour at 37° C., as measured by viral reverse transcriptase activity (See Example 1). In addition, aliquots of HIV derived from these H9 cell cultures lost the ability to replicate in culture when exposed to as little as 0.77 micrograms/ml of hypericin. Moreover, the addition of hypericin (at concentrations of up to 200 micrograms/ml) did not significantly affect the results of tests of routine clinical chemistries and hematological parameters.

Hypericin also inhibited cell-fusion between HIV-infected lymphocytes and healthy lymphocytes, which is another method of HIV-infection, (See Example 6) at 56–225 nanogram/ml concentrations. Pseudohypericin was also effective but at substantially higher (though still more than acceptably low from a toxicity point of view) concentrations.

The quantity of antiviral compound required to achieve effective inhibition of viral infectivity of the virus present in a given biological fluid may be achieved by using a single one of such compounds, or a combination of two or more of such compounds.

Naturally, it is desirable to employ the smallest possible quantity of the antiviral compounds of the invention that will provide a significant reduction or complete elimination of the infectivity properties of the target virus. In addition, one, two or more of the antiviral compounds can be employed together to inactivate any viruses present in a biological fluid. The precise antiviral compound or mixture of most effective antiviral compounds inhibiting a particular virus can be ascertained by routine experimentation well-known in the art.

The antiviral compounds of the present invention can be introduced into blood bags, or other blood storage containers either in the same manner as (or incorporated into) the usual anticoagulant solutions (citrate, phosphate, dextrose and adenosine-CPD-A) contained in such bags. Alternatively, the antiviral compounds of the invention may be injected into a blood bag a day or so prior to transfusion, or they can be incorporated in a separate device such as a satellite bag or satellite extension tube. Such devices are disclosed in U.S. Pat. Nos. 4,670,013, and 3,874,384 issued Jun. 2, 1987 and Apr. 1, 1975, respectively. In this way, sufficient quantities of the antiviral compounds of the present invention may be introduced into the main blood bag from the satellite or tube after it is filled with blood.

The art is replete with various types of blood bags made from a variety of substantially inert materials, such as polyvinyl chloride, polyethylene, ethylene ethylacrylate, ethylene vinyl acetate and other suitable relatively inert polymers and plastics (plasticized or not). A sufficient quantity of the antiviral compounds to terminate or significantly reduce viral infectivity can be instilled, delivered, introduced or deposited within such containers before or after introduction of the blood, blood component or other biological fluid therein. It is of course preferred to have the antiviral compound present in the biological fluid collection or storage device at the earliest possible stage (i.e. before addition of the potentially virus-contaminated fluid) in order to provide the best possible protection to persons handling or receiving the particular biological fluid.

The interior of virtually any container, device or arrangement used in containing, transferring, storing, processing or handling biological fluids can be provided with effective amounts of the antiviral compounds of the present invention except of course when such fluids are to be tested for viral infectivity directly (and not e.g. by detecting or measuring antibodies to a virus). The container can be sterile, as in the case of the interior of a blood bag used to collect blood for transfusions into patients, although this is not the case for all means for retaining biological fluids.

The antiviral compounds of the invention can be used for decontaminating articles, devices or equipment (e.g. chromatography equipment, laboratory equipment, etc.) that have come into contact with HIV or another retrovirus or virus.

The antiviral compounds may be added to blood vacuum storage tubes or containers in amounts effective to reduce or terminate retroviral or viral infectivity of any viral particles in such tubes.

The antiviral compounds may be employed in the present invention in pure form or in the form of pharmaceutically-acceptable salts thereof, and together with pharmaceutically-acceptable carriers or diluents. Non-limiting examples of such substances include carbohydrates, isotonic saline, propylene glycol, water, ethanol, isopropanol, albumin and/or other plasma protein components such as low density lipoproteins, high density lipoproteins and the lipids which with these serum proteins are combined or associated. Such lipids include phosphatidyl serine, phosphatidyl choline, phosphatidyl ethanolamine and neutral lipids such as triglycerides. Additional lipid carriers include tocopherol, retinoic acid and cyclodextrans.

The antiviral compound (or mixtures thereof) can be added to biological fluids in the form of a liquid solution, powder, tablet, capsule or any other form which can be solubilized in the biological fluid to be decontaminated. Such formulations have been described in U.S. patent application Ser. No. 084,008 filed Aug. 10, 1987 of Lavie et al. Liquid solutions are preferred because of their solubility in most of the biological fluids to be decontaminated.

The exact quantity of a particular antiviral compound (or mixtures thereof) that will be effective to provide a significant reduction, or complete elimination of the infectivity properties of a particular virus in a biological fluid will vary depending on the identity of the target virus, the quantity or amount of fluid to be treated and the time period during which the fluid is exposed to such compound(s). The minimum time during which a biological fluid must be exposed to (i.e. in contact with) one or more of the antiviral compounds of the invention to achieve inactivation of the infectivity properties of virus particles contained in such fluid is about five minutes.

In general, up to 100 mg and preferably between 1 mg and about 10 mg of the antiviral compounds may be employed to completely eliminate the infectivity properties of human retroviruses such as HIV in one unit of whole blood. Intravenous transfusion or administration of blood containing this level of hypericin for example should pose no serious toxicity or tolerance threat to human recipients of such transfused blood. Rodents (mice) exposed to intravenous doses of 100 micrograms of hypericin per mouse have not exhibited any toxic side effects. This correlates with a dose of approximately 25 mg i.v. in man, or twenty times the dose that would be received from a transfusion of 1 unit of whole blood containing 2.5 micrograms/ml hypericin. In addition, i.e. administration of 1.2 mg of hypericin in phosphate buffered saline (PBS) containing 10% ethanol to a mouse was not lethal. (Naturally, it is preferred to use the minimum amount of the antiviral compounds that is effective to terminate the infectivity of the target virus in a given biological fluid. The minimum effective amount required for abolishing infectivity of a particular viral species suspected to be present in a biological fluid can be easily determined through the exercise of routine experimentation.)

Therefore, the method of the present invention comprises incubating a biological fluid with an antiviral and/or anti-retroviral effective amount of an antiviral compound selected from the group consisting of hypericin, pseudohypericin, derivatives, analogs, isomers, homologs, salts and mixtures thereof (as illustrated in Appendix A) and thereby eliminating or significantly reducing the infectivity properties of viruses (including retrovirus species and HIV in particular) that may be present in the biological fluid.

Hypericin and pseudohypericin, the preferred antiviral compounds for use in practicing the method of the present invention, can be obtained by extraction from plants of the family-Hypericum as disclosed in U.S. patent application Ser. No. 084,008 filed Aug. 10, 1987 of Lavie et al. Alternatively, hypericin can be obtained by chemical synthesis as described in Cameron et al., *Austral. J. Chem.* 29: 1509, 1976 and Spitzner, D., *Angew. Chem. Int. Ed. Eng.* 16.: 46, 1977. Derivatives, isomers, homologs and analogs and salts of these compounds can be prepared in accordance with methods well-known in the art. The antiviral compounds identified in Appendix A are available from the National Cancer Institute at the National Institutes of Health (N.I.H.) Bethesda, Md.

Biological fluid containers, storage and transfer vessels (e.g. blood bags, vacuum transfer and storage tubes, etc.) for use in practicing the present invention (e.g. to inactivate virus present in whole blood or blood products that have been collected and stored for further transfusions or administration to human or animal patients) are commercially available from numerous hospital supply houses such as Baxter Hyland-Travenol (Deerfield, Ill.), Terumo (Tokyo, Japan), and American Hospital Supply Corp. (Evanston, Ill.). For example, blood storage bags are commercially available from Baxter Hyland Travenol. Vacuum blood storage tubes can be obtained from Becton-Dickinson (VACUTAINER ®, Rutherford, N.J.). Similar storage and collection devices are available from numerous sources.

When employed to inactivate retrovirus that may be present in biological fluids, antiviral concentrations ranging broadly between about 0.001 micrograms/ml and about 1000 micrograms/ml and preferably between 20 micrograms/ml and about 200 micrograms/ml of the antiviral compounds are effective to provide complete inactivation of any virus or retrovirus present in said fluid.

The compounds of the present invention may be impregnated into paper towelettes (available from L.N.I. Corp., Keyport, N.J.) and other sanitary wipes for use in decontaminating any spills or accidental exposure to infected biological fluids. It may also be desirable to add the antiviral compounds to containers used for storage of discarded needles and other equipment which may have contacted biological fluids in order to inactivate virus and/or retrovirus that may be present.

A further application of the present invention is useful in curbing sexual transmission of viral and/or retroviral infections. In this embodiment, an effective amount to inactivate the target virus (or retrovirus and especially HIV) of the active compounds is applied to the surfaces of contraceptive devices, e.g. condoms, diaphragms, etc. or incorporated as a constituent in contraceptive foams, suppositories, jellies and the like. The antiviral compounds are preferably incorporated in the same manner and at the same time as the conventional lubricants and spermicidal agents employed with such contraceptive devices.

Effective amounts of the antiviral compounds of the invention may also be incorporated as an ingredient in vaginal jellies and/or lubricant compositions.

The antiviral compounds may be incorporated in condoms by admixture with the well-known lubricants and spermicide compositions applied to the surface of condom products to inactivate, e.g. HIV or Herpes Simplex Virus that may be present in the vaginal area during intercourse. Condoms have been recommended by the Surgeon General as a means of preventing the spread of HIV by sexual contact. However, condoms have a relatively high failure rate and hence cannot be relied on to completely protect against exposure to HIV (or other retroviral or viral) infection. Since hypericin inactivates free viral particles as well as virus present in infected cells at concentrations as low as 0.77 micrograms/ml (0.00077%, wt/vol), dilution of the antiviral compounds by vaginal or seminal secretions should not abrogate their antiviral and/or anti-retroviral effect.

Contraceptive shields such as condoms and diaphragms are made from a variety of synthetic, natural and semi-synthetic materials including for example nonylphenoxyl polyethoxyethanol latex rubber, plastic, collagen or sheep caecum and are widely available. In many instances, lubricant compositions e.g. polyethylene glycol (MW 400), nonylphenoxypolyethoxyethanol (which also has spermicidal properties) and other polyethoxylated nonyl phenols e.g. triisopropyl phenoxypolyethoxyethanol as well as dimethylpolysiloxane or other surface wetting agents or emulsifying agents are present on the surface of prophylactics or condoms. Known vaginal jellies or spermicidal suppositories contain polyethylene glycol (MW < 4000) and a spermicide e.g. triisopropylene phenoxy polyethoxyethanol, cetylpryidinium bromide or dodecaethyleneglycol monolaurate are commercially available. The antiviral compounds of the present invention can be incorporated in the lubricant compositions that are applied to diaphragms and condoms, or as a constituent in vaginal creams and jellies to afford a measure of protection against infection by HIV or Herpes Simplex Virus. The efficacy of using hypericin against HIV present in semen is illustrated in Example 4. The effectiveness of hypericin incorporated as an element of the lubricant employed in condoms will be further assessed using an in vitro model of simulated sexual intercourse developed by Rietmeijer et al., infra as described in Example 4 below. Based upon the data presented in Example 1 below it is anticipated that hypericin will completely abrogate viral infectivity in semen at concentrations of 0.77 micrograms/ml or greater. Other antiviral compounds (e.g. as described in Appendix A) can also be employed at concentrations adjusted in accordance with the specific antiviral/anti-retroviral activity of each compound or mixture.

Another important embodiment of the present invention involves combatting viral and retroviral infections in animals and the transmission of such infections associated with transfer of contaminated blood or other biological fluids (such as semen during artificial insemination) to such animals. Effective amounts of the antiviral compounds can be incorporated in the biological fluid to be transferred. In addition, all of the prophylactic uses of the antiviral compounds described in connection with human health care are applicable in connection with care of animals and the viruses and retroviruses that infect domesticated animals such as dogs, cats, goats, sheep, cows, horses, etc.

The invention is further described below in specific working examples which are intended to illustrate the invention without limiting its scope.

EXAMPLE 1

Hypericin (Hy) and Pseudohypericin (Ps) Inactivates HIV in Blood and Other Body Fluids In order to show the effectiveness of the compounds of the present invention in the inactivation of HIV, blood was obtained from an HIV sero-positive patient and treated with hypericin and pseudohypericin at various concentrations for 1 hour at 37° C. and incubated with uninfected H9 cells in culture. Thereafter, reverse transcriptase enzymatic activity was determined as disclosed in U.S. patent application Ser. Nos. 084,008 and 172,064 filed Aug. 10, 1987 and Mar. 23, 1988, respectively. The results are shown in FIG. 1.

Figure 1:
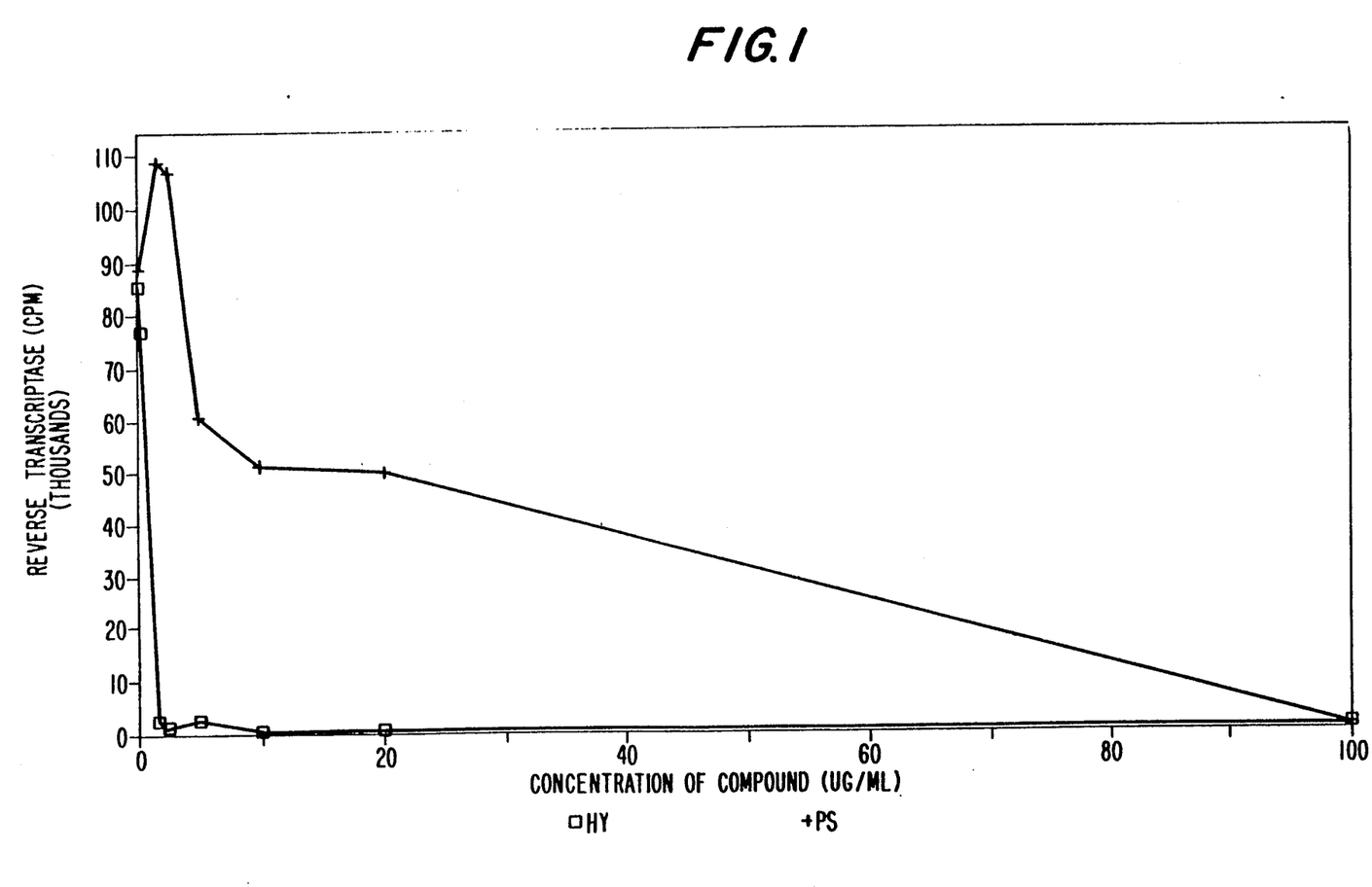
FIG. 1 is a graph showing the inactivation of HIV isolated from an AIDS patient after incubation of the virus with hypericin or pseudohypericin in vitro.

FIG. 1 shows the inactivation of HIV isolated from an infected individual using concentrations ranging between 0.77 micrograms/ml and 100 micrograms/ml of Hy or Ps, respectively. The results are shown in FIG. 1.

Figure 2:
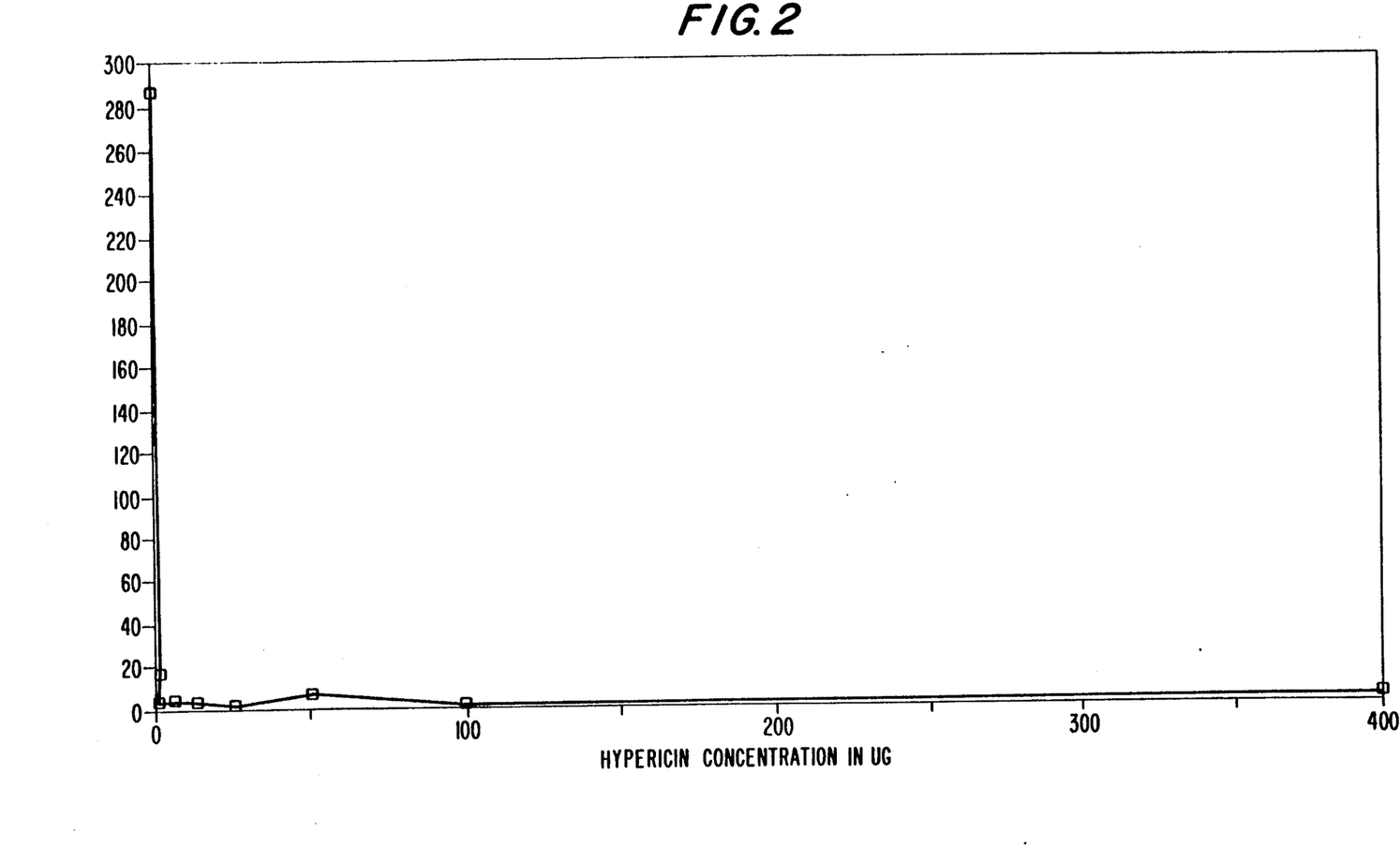
FIG. 2 is a graph showing the effect of hypericin and pseudohypericin on the infectivity of HIV cultured from an AIDS patient.

In FIG. 1, open squares represent hypericin-treated and pluses represent pseudohypericin treated HIV. As can be seen in FIG. 1, no reverse transcriptase was detected in a virus cultivated at concentrations of Hy higher than 2.5 micrograms/ml or Ps concentrations above 100 micrograms/ml. Inactivation of the reverse transcriptase activity of the virions was not a result of a direct inhibition of reverse transcriptase activity per se, as incubation of either compound directly with purified reverse transcriptase from either avian myeloblastosis virus or murine leukemia virus had no effect on enzyme activity. Furthermore, aliquots of HIV derived from these H9 cell cultures lost the ability to replicate in culture when exposed to as little as 0.77 micrograms/ml of hypericin. This result is shown in FIG. 2. This result shows that hypericin does not interfere strictly with the ability of viral reverse transcriptase to generate cDNA, except in the presence of virus particles or cells.

EXAMPLE 2

Hypericin Does Not Interfere With the Results of Standard Clinical Tests on Blood and Other Body Fluids Triplicate samples of blood were drawn from two normal individuals directly into vacuum tubes. Into one set of tubes was added hypericin dissolved in 10% ethanol, 40% propylene glycol, 50% water to a final concentration of hypericin of 0.1 micrograms/ml of blood. A second set of tubes received hypericin at 1.0 micrograms/ml of blood. The final concentration of ethanol was 0.01% and of propylene glycol 0.04% in each sample, respectively. The third set served as an untreated control. Hypericin-treated and untreated samples were taken directly to a clinical laboratory for testing of standard blood chemistries, complete blood count, and a coagulation profile. The results of parallel assays of these blood parameters in two different normal individuals are shown in Tables 2 and 3:

TABLE 2

Addition of hypericin to whole blood - lack of effect on standard blood chemistries and hematologic parameters

| Subject #1 "LL" | control | 0.1 micrograms/ml | 1.0 micrograms/ml |
|---|---|---|---|
| WBC/cu mm | 8.3 | 8.1 | 8.0 |
| lymphs | 34.5% | 34.9% | 32.9% |
| monos | 5.0% | 4.2% | 5.5% |
| neutr | 60.5% | 60.9% | 61.6% |
| Hct | 46.6% | 46.7% | 47.6% |
| Hb (gm/dl) | 15.6 | 15.8 | 16.0 |
| MCV | 91.2 | 91.0 | 91.1 |
| MCH | 30.5 | 30.8 | 30.6 |
| MCHC | 33.5 | 33.8 | 33.6 |
| plts ($\times 10^{-3}$) | 323 | 321 | 329 |
| ESR mm/hr | 3 | 5 | 4 |
| PT | 10.8/10.8 | 10.8/10.8 | 10.8/10.9 |
| APTT | 28.2/28.3 | 28.5/28.6 | 28.1/28.2 |
| $Na^+$ (meq/l) | 142 | 140 | 137 |
| $K^+$ (meq/l) | 4.2 | 4.2 | 4.3 |
| $Cl^-$ (meq/l) | 106 | 106 | 106 |
| $CO_2$ (meq/l) | 29 | 28 | 28 |
| BUN (mg/dl) | 13 | 13 | 12 |
| Creat (mg/dl) | 0.9 | 0.9 | 0.9 |
| Glucose (mg/dl) | 107 | 107 | 105 |
| Bilirubin (mg/dl) | 0.5 | 0.5 | 0.5 |
| Bilirubin (direct) | 0.0 | 0.1 | 0.1 |
| uric acid (mg/dl) | 5.6 | 5.7 | 5.6 |
| alk phos (IU/l) | 74 | 76 | 75 |
| SGOT (IU/l) | 16 | 19 | 15 |
| LDH (IU/l) | 143 | 154 | 153 |
| total protein (gm/dl) | 7.4 | 7.5 | 7.5 |
| albumin (gm/dl) | 4.5 | 4.8 | 4.8 |
| $Ca^+$ (mg/dl) | 10.0 | 10.1 | 10.2 |
| phosphate (mg/dl) | 3.6 | 3.7 | 3.6 |
| cholesterol (mg/dl) | 249 | 255 | 258 |

TABLE 3

Addition of hypericin to whole blood - lack of significant effect on standard blood chemistries and hematologic parameters

| Subject #2 "BL" | control | 0.1 micrograms/ml | 1.0 micrograms/ml |
|---|---|---|---|
| WBC/cu mm | 6.9 | 6.7 | 6.4 |
| lymphs | 33.8% | 33.1% | 32.0 |
| monos | 3.1% | 4.9% | 5.2% |
| neutr | 63.1% | 62.0% | 62.8% |
| Hct | 38.8% | 37.8% | 37.3% |
| Hb (gm/dl) | 13.3 | 13.0 | 12.9 |
| MCV | 91.4 | 91.4 | 91.3 |
| MCH | 31.3 | 31.4 | 31.6 |
| MCHC | 34.2 | 34.4 | 34.6 |
| plts ($\times 10^{-3}$) | 342 | 317 | 317 |
| ESR mm/hr | 1 | 1 | 1 |
| PT | 11.7/11.7 | 11.6/11.6 | 11.7/11.7 |
| APTT | 27.7/27.7 | 27.2/27.3 | 27.9/27.8 |
| $Na^+$ (meq/l) | 140 | 140 | 141 |
| $K^+$ (meq/l) | 4.5 | 4.4 | 4.5 |
| $Cl^-$ (meq/l) | 109 | 108 | 108 |
| $CO_2$ (meq/l) | 27 | 27 | 27 |
| BUN (mg/dl) | 10 | 9 | 8 |
| Creat (mg/dl) | 0.6 | 0.7 | 0.6 |
| Glucose (mg/dl) | 98 | 96 | 95 |
| Bilirubin (mg/dl) | 0.7 | 0.5 | 0.5 |
| Bilirubin (direct) | 0.0 | 0.1 | 0.1 |
| uric acid (mg/dl) | 4.4 | 4.2 | 4.1 |
| alk phos (IU/l) | 51 | 51 | 52 |
| SGOT (IU/L) | 17 | 15 | 14 |
| LDH (IU/L) | 115 | 110 | 97 |
| total protein (g/dl) | 6.4 | 6.4 | 6.3 |
| albumin ((gm/dl) | 4.4 | 4.5 | 4.4 |
| $Ca^+$ ((mg/dl) | 9.6 | 9.5 | 9.5 |
| phosphate (mg/dl) | 3.2 | 3.0 | 3.1 |
| cholestrol | 133 | 133 | 131 |

TABLE 3-continued

Addition of hypericin to whole blood - lack of significant effect on standard blood chemistries and hematologic parameters

| Subject #2 "BL" ((mg/dl) | control | 0.1 micrograms/ml | 1.0 micrograms/ml |
|---|---|---|---|

As can be seen from the results presented in Tables 2 and 3, hypericin at concentrations of 1.0 and 0.1 micrograms/ml had no significant effect on any of the parameters studied.

Analogous experiments to assess the effect of hypericin on routine clinical chemistries and hematologic parameters were determined in a commercial laboratory on mouse blood using higher concentrations of hypericin. Eight blood samples drawn in parallel were treated with hypericin ranging in concentration from 2.5 micrograms/ml to 200 micrograms/ml of whole blood. The results of these studies are shown in Tables 4 and 5, below.

ples. Sample 1 will serve as the untreated control sample. Into Samples 2 and 3 will be added hypericin to a final concentration of 1.0 micrograms/ml and 2.5 micrograms/ml, respectively. All three urine samples will be submitted to a clinical laboratory for routine urinalysis testing including specific gravity measurements, cell count, total protein, glucose and creatine determinations. No significant difference between the hypericin-treated and untreated samples is expected.

In an analogous experiment on cerebrospinal fluid (CSF), CSF will be collected from an individual undergoing a diagnostic lumbar puncture. The CSF will be divided into three samples. Sample 1 will serve as the untreated control sample. Samples 2 and 3 will be adjusted to contain hypericin at concentrations of 1.0 micrograms/ml and 2.5 micrograms/ml, respectively. All 3 CSF samples will be submitted for analysis of total protein, glucose and cell count. No significant difference between hypericin-treated and untreated samples is expected.

Additional experiments on blood, urine and CSF will be performed to assess the effect of the antiviral com-

TABLE 4

Effect of hypericin on hematologic parameters in normal mouse blood

| amount of hypericin: | 0 | | 200 μg | | 100 μg | | 50 μg | | 25 μg | | 10 μg | | 5.0 μg | | 2.5 μg | |
|---|---|---|---|---|---|---|---|---|---|---|---|---|---|---|---|---|
| subject # | 1 | 2 | 3 | 4 | 5 | 6 | 7 | 8 | 9 | 10 | 11 | 12 | 13 | 14 | 15 | 16 |
| WBC/cumm | 4.8 | 4.7 | 4.4 | 4.6 | 4.9 | 5.0 | 4.8 | 4.8 | 4.7 | 4.7 | 4.5 | 4.5 | 4.7 | 4.5 | 4.6 | 4.8 |
| Hematocrit | 38.1 | 37.7 | 37.5 | 34.6 | 37.8 | 38.4 | 38.1 | 38.0 | 37.7 | 37.9 | 37.8 | 37.8 | 38.5 | 38.5 | 38.3 | 37.8 |
| Hb (gm, dl) | 12.8 | 12.9 | 12.6 | 12.7 | 12.8 | 13.2 | 12.8 | 12.8 | 12.8 | 12.8 | 12.8 | 12.3 | 12.9 | 12.4 | 12.7 | 12.7 |
| platelets ($\times 10^{-4}$/cumm) | 9.1 | 9.2 | 10.4 | 10.6 | 10.1 | 9.9 | 9.6 | 9.6 | 9.2 | 10.1 | 10.0 | 10.1 | 8.8 | 9.8 | 9.5 | 9.7 |
| retics (%) | 1.6 | 1.5 | 2.8 | 0.6 | 0.8 | 0.7 | 1.4 | 2.5 | 0.8 | 0.3 | 1.7 | 0.5 | 2.2 | 2.0 | 1.5 | 2.3 |

TABLE 5

Effect of hypericin on blood chemistries of normal mice

| amount of hypericin: | 0 | | 200 μg | | 100 μg | | 50 μg | | 25 μg | | 10 μg | | 5.0 μg | | 2.5 μg | |
|---|---|---|---|---|---|---|---|---|---|---|---|---|---|---|---|---|
| subject # | 1 | 2 | 3 | 4 | 5 | 6 | 7 | 8 | 9 | 10 | 11 | 12 | 13 | 14 | 15 | 16 |
| calcium (mg/dl) | 6.7 | 6.6 | 6.6 | 6.6 | 6.6 | 6.6 | 6.6 | 6.8 | 6.7 | 6.3 | 6.7 | 6.7 | 7.0 | — | 6.7 | 5.4 |
| phosphorous (mg/dl) | 8.1 | 7.9 | 7.9 | 8.0 | 8.2 | 8.0 | 8.3 | 8.2 | 8.2 | 8.1 | 8.2 | 8.1 | 8.1 | — | 8.1 | 7.2 |
| glucose (mg/dl) | 114 | 110 | 122 | 111 | 113 | 1.9 | 113 | 114 | 111 | 110 | 113 | 113 | 112 | | 113 | 68 |
| BUN (mg/dl) | 18 | 18 | 18 | 18 | 18 | 17 | 18 | 18 | 18 | 18 | 18 | 18 | 18 | — | 18 | 17 |
| uric acid mg/dl | 2.5 | 2.6 | 3.8 | 3.6 | 3.2 | 3.1 | 3.0 | 2.8 | 3.9 | 3.8 | 2.9 | 3.0 | 2.7 | | 2.6 | 2.8 |
| sodium meq/l | 151 | 148 | 145 | 147 | 149 | 146 | 148 | 148 | 146 | 144 | 148 | 148 | 150 | — | 150 | 138 |
| chloride meq/l | 114 | 113 | 110 | 111 | 112 | 11 | 113 | 113 | 111 | 110 | 112 | 112 | 113 | — | 113 | 102 |
| creatinine (mg/dl) | 0.4 | 0.4 | 0.4 | 0.4 | 0.4 | 0.4 | 0.4 | 0.4 | 0.3 | 0.3 | 0.3 | 0.3 | 0.4 | — | 0.4 | 0.4 |
| cholesterol (mg/dl) | 149 | 147 | 155 | 157 | 153 | 151 | 152 | 150 | 166 | 162 | 155 | 155 | 156 | — | 149 | 143 |
| triglycerides (mg/dl) | 90 | 83 | 92 | 89 | 92 | 87 | 61 | 62 | 80 | 84 | 67 | 64 | 85 | — | 80 | 77 |
| iron (mog/dl) | 225 | 221 | 211 | 215 | 220 | 216 | 220 | 221 | 218 | 219 | 218 | 220 | 220 | — | 219 | 169 |
| total protein (g/dl) | 7.3 | 5.9 | 6.8 | 6.4 | 6.5 | 6.1 | 6.5 | 6.5 | 6.8 | 6.9 | 6.5 | 6.5 | — | — | 6.0 | 5.8 |
| globulins (g/dl) | 3.9 | 2.5 | 3.3 | 2.9 | 3.0 | 2.7 | 3.0 | 3.0 | 3.1 | 3.3 | 3.0 | 3.0 | — | — | 2.6 | 3.2 |
| albumin (g/dl) | 3.4 | 3.4 | 3.5 | 3.5 | 3.5 | 3.4 | 3.5 | 3.5 | 3.7 | 3.6 | 3.5 | 3.5 | 3.5 | — | 3.4 | 2.6 |
| total bilirubin (mg/dl) | 0.8 | 0.7 | 1.1 | 1.1 | 1.0 | 1.0 | 0.8 | 0.9 | — | 0.9 | 0.8 | 0.9 | 0.8 | — | 0.8 | 1.2 |
| alk. phos. (IU/l) | 139 | 141 | 139 | 140 | 140 | 138 | 141 | 141 | 136 | 134 | 138 | 140 | 140 | — | 140 | 121 |

As can be seen in the data presented in Tables 4 and 5 above, treatment of blood with hypericin at concentrations of up to 200 micrograms/ml did not significantly affect the results of these common hematological parameters as compared with untreated samples.

Based on the above data, it is expected that hypericin will be shown to have no effect on the commonly measured clinical parameters of urine and cerebrospinal fluid by the following experiments. Urine will be obtained from a normal individual and divided into 3 sampounds on bacteriologic studies of these body fluids. Patients suspected of having active bacterial or fungal infections will be studied. Biological fluids derived from such patients will be divided into 3 samples, as outlined above. Sample 1 will serve as the untreated control. Into Samples 2 and 3 will be added 0.1 micrograms/ml and 1.0 micrograms/ml of hypericin, respectively. Results of routine bacteriologic studies for bacterial and fungal growth will be compared in these three samples. No significant difference is expected between hypericin-treated and untreated samples.

EXAMPLE 3

The Use of Hypericin to Inactivate HIV, HTLV-1 and Other Human Retroviruses in Human Blood Components Used for Transfusion Over 1,000 cases of HIV infection have been reported in the United States in recipients of transfusions of blood products contaminated with HIV. The following experiments will be performed to demonstrate the feasibility of using hypericin to inactivate HIV present in human blood products. Two half unit (250 ml) samples of blood will be collected from a normal blood donor. Sample 1 will be used as a control and will be processed unaltered. Sample 2 will be collected into a blood bag containing 625 micrograms/ml of hypericin (final concentration of hypericin 2.5 micrograms/ml blood). Ten milliliters will be removed from each sample for type and cross matching, Coombs testing, and viral serologic studies for HIV and hepatitis B virus. The 2 samples will then be processed in parallel by standard methods to obtain packed red cells (RBC), platelet concentrate, and fresh plasma (as described in Mollison, P. L., et al., in *Blood Transfusion in Clinical Medicine*, 8th Edition, Blackwell Scientific Publications, Oxford, 1987. Packed red cells will be stored for 28 days in CPD (Citrate-Phosphate-Dextrose), as described in Mollison, P. L., et al., supra, p. 812, and in vitro RBC survival and viability will be tested. In addition, hypericin-treated RBC's will be labeled with $^{51}$Cr as described in Mollison, P. L. et al., supra, pp. 807–808 and autologous red cell survival studies will be performed in vivo (Mollison, P. L., et al., supra, pp. 102–105). No significant differences between hypericin treated and untreated blood are anticipated based upon the lack of toxicity of the aromatic polycyclic dione compounds on mammalian and human cells. Red cell survival of hypericin-treated blood is expected to be in the normal range.

Platelet concentrates from Sample 1 (control) and Sample 2 (hypericin-treated) will be prepared and stored at room temperature with constant agitation for 5 days, as described in Mollison, P. L., et al., supra, p. 807. Samples will then be studied in parallel for standard tests of platelet aggregation in response to ADP, epinephrine, thrombin, collagen, and ristocetin. Fresh frozen plasma derived from Samples 1 and 2 will be likewise studied using standard coagulation parameters, prothrombin time and activated partial thromboplastin time, using procedures well known in the art.

EXAMPLE 4

Use of Hypericin in Condoms and Spermicide Compositions to Inactivate HIV and Other Human Retroviruses Fresh semen samples will be obtained from normal donors and mixed with infectious HIV preparations obtained from cultured H9 cells ($10^4$ infectious units per ml). Virally contaminated semen samples will then be exposed to hypericin at concentrations ranging between 0.5 micrograms/ml and 2.5 micrograms/ml. After 5 minutes of incubation, an aliquot of each sample will be added into culture with H9 cells. After an appropriate period of time (e.g. 1 hour at 37° C.), cultures will be assayed for reverse transcriptase activity. It is expected that hypericin will completely inactivate viral infectivity in semen at concentrations of 0.77 micrograms/ml or higher as was found in Example 1 above. Analogous experiments will be performed by mixing hypericin with commercially available condom spermicidal lubricants or vaginal spermicides.

The effectiveness of hypericin incorporated into condoms will be further assessed by using the in vitro model of simulated intercourse developed by Rietmeijer et al (*J. Amer. Med. Assoc.* 259: 1851–1853, 1988). Condoms will be mounted on an artificial penis and placed in a glass cylinder. An HIV inoculum and control HIV-free medium will be placed on each surface of the condom, respectively. Intercourse will be simulated by pumping the artificial penis up and down in a cylinder before and after deliberate rupture of the condom. Samples will be taken from outside and inside the condom, before and after rupture and in the presence or absence of hypericin at various concentrations. The samples will be tested for viral reverse transcriptase activity and viral infectivity. In this fashion, the effectiveness of hypericin at inhibiting HIV infectivity in the condom environment can be assessed.

EXAMPLE 5

Inhibition of Budding Virus from Infected Cells by Hypericin

This test was designed to show that hypericin inhibits virus budding from virus-infected cells.

AQR (murine leukemia) cells producing Radiation Leukemia Virus (prepared as described in Meruelo, D., *J. Exp. Med.* 149: 898–909, 1979; and Bach, R. G. et al., *J. Exp. Med.* 160: 270–285, 1984) were incubated for 1 hour with various concentrations of synthetic hypericin (micrograms/ml shown in FIG. 3). The cells were then washed four times with phosphate buffer saline and incubated in fresh culture medium for 24 or 48 hours. Supernatants were then collected, pelleted (at $1000 \times g$) for 15 minutes to remove whole cells and then repelleted at $100,000 \times g$ for 1 hour to collect virus particles. The second pellet was used for a reverse transcriptase assay, conducted as described in U.S. application Ser. No. 084,008 (Aug. 10, 1987) and 172,064 (Mar. 23, 1988).

Figure 3:
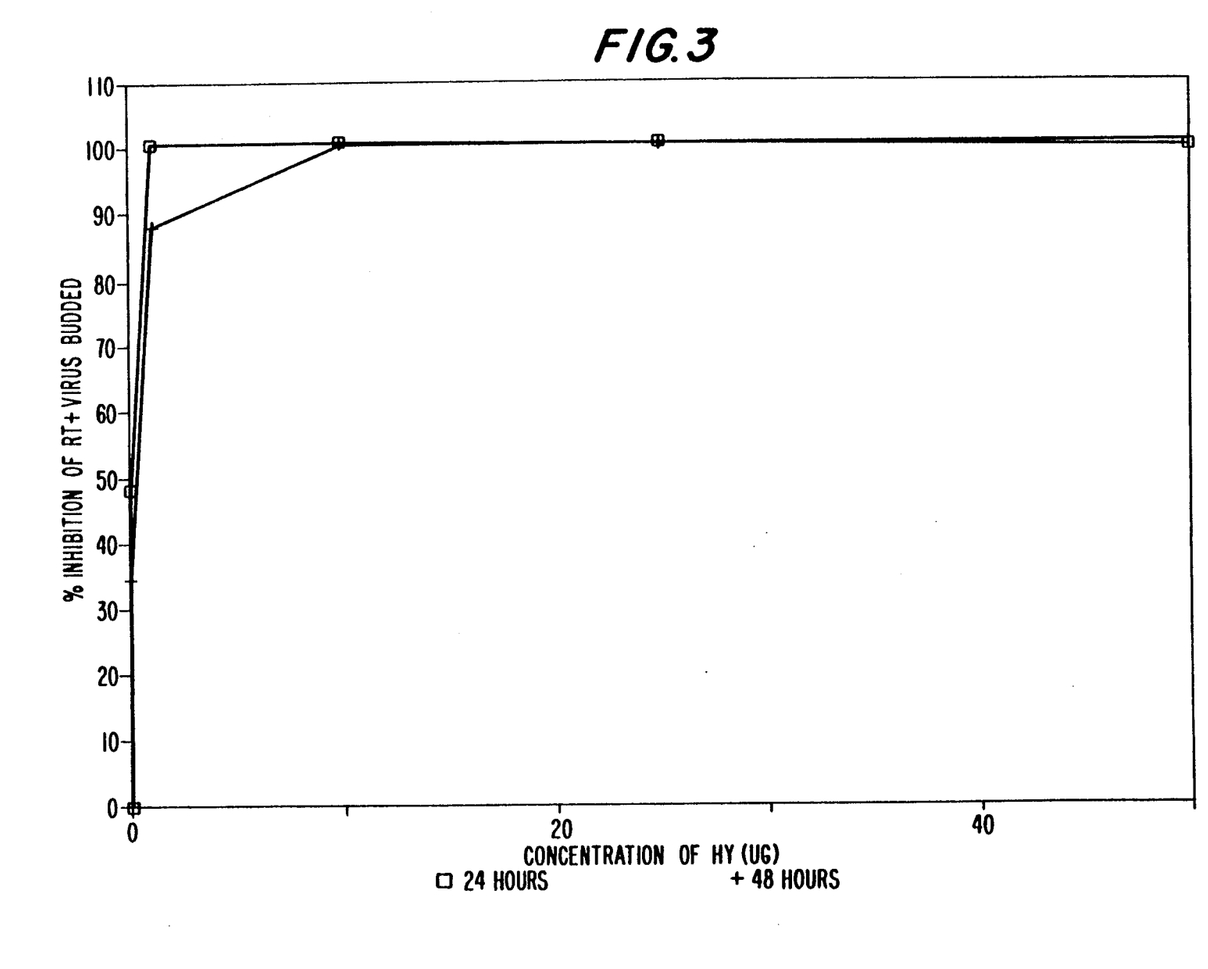
FIG. 3 is a graph showing inhibition by hypericin of the ability of Radiation Leukemia Virus particles to bud from infected AQR cells.

The results of the reverse transcriptase assay are plotted in FIG. 3. Therein, it is shown that virus budding from the AQR cells was completely inhibited even after 24 hours (open squares) at a hypericin concentration of 10 micrograms/ml. In fact, incubation of free, i.e. not budding, HIV virus with hypericin for as little time as it took to add the compound to cells and centrifuge the preparation still showed a significant inhibition of virus infectivity and inhibition was complete at 10 and even at 5 minutes. Thus, the minimum incubation period that would destroy the ability of HIV-infected cells to participate in propagation of the HIV infection is likely to be much smaller than the 24 hours employed as the minimum waiting period in this assay.

EXAMPLE 6

Inhibition of HIV Induced Syncytia Formation by Hy and Ps

A prominent feature of HIV is its ability to bind to and fuse with target cells. HIV binds to cells through the specific interaction of the envelope glycoprotein gp120 with a high affinity binding site on the human CD4 surface antigen, the cellular receptor for the virus. In addition, in vitro HIV-mediated cell fusion results in the formation of multi-nucleated giant cells or syncytia. In vitro fusion is thought to occur in an analogous manner as virus entry in vivo.

In order to assess the effects of Hy and Ps on the ability of HIV to form syncytia, the following experiments were performed. For the analysis of HIV-1, an entry syncytia assay was performed by co-culturing H9 cells (described in Popovic, M. et al. *Science* 224: 497–500, 1984) infected with the IIIb isolate of HIV with uninfected Supt-1 cells (Walker, B. D. et al. *Proc. Nat. Acad. Sci.* (USA) 84: 8120–8124, 1987) as the target cell. HIV-2 was tested using HUT78 cells (obtained from the National Institute of Health by reference to Depository Catalog, Reagent Program, Bethesda, Md.) infected with the ROD-2 isolate of HIV-2 co-cultured with uninfected H9 target cells. The infected cells were plated in 96 well plates ($10^4$ cells per well in RPM1 1640 medium with 10% fetal calf serum) and incubated with or without dilutions of Ps or Hy for 30 minutes at 37° C. $1 \times 10^5$ target cells were then added per well and the number of syncytia were quantitatively and qualitatively determined after 24 hours. The results are presented in Table 6 below.

TABLE 6
Ability of Compounds to Inhibit Syncytia Formation

| | Activity of Hypericin (Concentration in nanograms) | | | | | | | | |
|---|---|---|---|---|---|---|---|---|---|
| | 1800 | 900 | 450 | 225 | 112 | 56 | 28 | 14 | 7 |
| HIV-1 | 0 | 0 | 0 | 0 | 0 | 0 | 3L | 4L | 4L |
| Control | 4L | 4L | 4L | 4L | 4L | 4L | 4L | 4L | 4L |
| HIV-2 | 0 | 0 | 0 | 0 | 1S | 3M | 4L | 4L | 4L |
| Control | 4L | 4L | 4L | 4L | 4L | 4L | 4L | 4L | 4L |
| HIV-1 env | 0 | 0 | 0 | 0 | 3M | 4L | 4L | 4L | 4L |
| Control | 4L | 4L | 4L | 4L | 4L | 4L | 4L | 4L | 4L |

| | Activity of Pseudohypericin (Concentration in nanograms) | | | | | | | | |
|---|---|---|---|---|---|---|---|---|---|
| | 3000 | 1500 | 750 | 375 | 188 | 94 | 47 | 24 | 12 |
| Assay HIV-1 | 1S | 3M | 4L | 4L | 4L | 4L | 4L | 4L | 4L |
| Control | 4L | 4L | 4L | 4L | 4L | 4L | 4L | 4L | 4L |
| HIV-2 | 2S | 2S | 3M | 4L | 4L | 4L | 4L | 4L | 4L |
| Control | 4L | 4L | 4L | 4L | 4L | 4L | 4L | 4L | 4L |
| HIV-1 env | 1S | 3L | 4L | 4L | 4L | 4L | 4L | 4L | 4L |
| Control | 4L | 4L | 4L | 4L | 4L | 4L | 4L | 4L | 4L |

In Table 6, the number of syncytia were scored numerically from 0 to 4 with 4 being multiple syncytia widely distributed and 0 indicating no syncytia observed.

The size of the syncytia was also recorded as S=small, M=medium, L=large.

From the results presented in Table 6 above it can be seen that hypericin was able to inhibit syncytia formation at doses of 56–225 ng/ml whereas pseudohypericin required doses 20–60 fold higher to achieve a similar degree of inhibition (Table 6).

Also tested in a syncytia assay was a constructed cell line expressing only the envelope proteins of HIV-1 type IIIb isolate (Walker, B. D. et al., supra). These cells, designated HIV-1 env in Table 6, were treated with the indicated concentrations of Ps or Hy and incubated with uninfected Supt-1 target cells as above. In these assays, as in the live virus assays, hypericin was again more effective than pseudohypericin in mediating inhibition of the viral entry process (Table 6).

APPENDIX A

Listed below are a series of compounds which, due to their structural similarity with hypericin, are expected to be active against viruses present in biological fluids.

These compounds are available upon request from the National Cancer Institute, Bethesda, Md. and their properties has been described in Weiss, U. et al. *Progress in Chemistry of Organic Natural Products* 52: 1–71, 1987.

1. CAS Registry No. 14343921
2. CAS Registry No. 6336841
3. CAS Registry No. 14642729
4. CAS Registry No. 6336874
5. CAS Registry No. 6941475
6. CAS Registry No. 4478766
7. CAS Registry No. 2013583
8. CAS Registry No. 667914
9. CAS Registry No. 434855
10. CAS Registry No. 3438082
11. CAS Registry No. 24541193
12. CAS Registry No. 10395025
13. [NSC No. 123399-N]

14. CAS Registry No. 69544850
15. CAS Registry No. 55043419
16. CAS Registry No. 71205384
17. CAS Registry No. 52236541
18. [NSC No. 231579-Y]

19. [NSC No. 241039-I]

20. CAS Registry No. 27575468
21. [NSC No. 308787-V]

-continued

22. [NSC No. 308805-Q]

23. [NSC No. 308814-Z]

-continued

24. CAS Registry No. 14343954
25. Rondomycin, 2-Naphthacenecarboxamide, NSC No. 356465-U

26. CAS Registry No. 81092844
27. CAS Registry No. 81092855
28. [NSC No. 507458-S]

In addition, due to their structural similarity with the aromatic polycyclic diones of the present invention, the anthraquinone compounds listed below are also expected to be active against viruses present in biological fluids. The properties of these compounds, 6-10 and 13-25, have been described in Banks, H. J. et al., *Aust. J. Chem.* 29: 1509-1521,

|  | $R^1$ | $R^2$ |
|---|---|---|
| (7) | Me | Me |
| (8) | Me | $CO_2H$ |
| (9) | $CO_2H$ | $CO_2H$ |
| (10) | Me | $CH_2OH$ |

The synthesis and/or isolation of compounds 6-10 and 13-25 listed above are described in the following references.

6. Skyrin: Auterhoff, H. et al. Arch. Pharm. 295: 850, 1962.
7. Hypericin: Brockmann, supra.
8. Hypericin monocarboxylic acid: Thompso, R. H. Naturally Occurring Quinones, 2nd Ed. Academic Press, London, 1971; Banks, H. J. et al., Insect Biochem. 3: 139, 1973; Brown, K. S., Chem. Soc. Rev. 4: 263, 1973; Anslow, W. K. et al., Biochem. J. 34: 159, 1940.
9. Hypericin dicarboxylic acid: Banks H. J. et al., Aust. J. Chem. 29: 1509-1521, 1976.
10. Banks et al., supra.
13. Protohypericin:
14. Banks et al., supra.
15. Banks et al., supra.

-continued

16. Banks et al., supra.
17. Emodin bianthrone: Anslow, W. K. et al., supra.
18. Emodinic acid bianthrone: Anslow, W. K. et al., supra.
19. Anslow, W. K. et al., supra.
20. Banks et al., supra.
21. Isohypericin: Steglich, W. et al., Angew. Chem. Int. Ed. Engl. 12: 79, 1973.
22. 10-peroxy-9-anthrone: Bedford, C. T., J. Chem. Soc. C.: 2514, 1968.
23. Penicilliopsin: Banks et al., supra.
24. Hyperico-dehydrodianthrone; Banks et al., supra.
25. Banks et al., supra.

Moreover, the compounds listed below are also related to hypericin and therefore expected to possess antiviral activity.

The synthesis of the above compounds has been described in Brockmann, H. M., in *Progress in Organic Chemistry*, Vol. I, Cook, J. W. ed., p 64–82, 1952.

C₆H₅CO₂ instead of OH

R = CH₃

R' = H, R'' = CH₃

OH, R', R'' = H

The synthesis of the above compounds has been described in Brockmann, H. et al., *Tetrahedron Letters* 23: 1991-1994, 1974.

-continued

R = —H

R = —CH₃

R = —H

The synthesis of the above compounds has been described in Brockmann, H. et al., U.S. Pat. No. 2,707,704 issued May 3, 1955.

What is claimed is:

1. An article of manufacture for holding a biological fluid and including means to inactivate any virus in such fluid, comprising:
   container means for holding a biological fluid which may be contaminated with a virus, and
   an effective amount for inactivating said virus of at least one antiviral compound selected from the group consisting of antiviral effective aromatic polycyclic diones; antiviral effective analogs, isomers, homologs and derivatives of said aromatic polycyclic diones; physiologically acceptable salts of said diones, analogs, isomers, homologs and derivatives; and mixtures of said diones, analogs, isomers, homologs, derivatives and salts, said compound being present in said container means for contacting said fluid when said fluid is introduced into said container means.

2. The article of manufacture of claim 1, wherein said effective amount is a quantity of said antiviral compound that is sufficient to abolish the infectivity of the Human Immunodeficiency Virus present in a volume of said fluid retained in said container.

3. An article in accordance with claim 1, wherein said antiviral compound is selected from the group consisting of hypericin; antiviral effective analogs, isomers, homologs and derivatives of said hypericin; physiologically acceptable salts of said hypericin, analogs, isomers, homologs and derivatives; and mixtures of said hypericin, analogs, isomers, homologs, derivatives and salts.

4. An article in accordance with claim 3, wherein said antiviral compound is hypericin or a physiologically acceptable salt thereof.

5. An article of manufacture in accordance with claim 1, wherein said effective amount is a quantity which is not substantially larger than the minimum amount of said antiviral compound that is effective to terminate any infectivity of the target virus present in a volume of the biological fluid retained in said container means.

6. An article of manufacture in accordance with claim 1, wherein said container means is other than laboratory glassware.

7. An article of claim 1 wherein said compound is present in solid or liquid form.

8. The article of manufacture of claim 7, wherein said effective amount is a quantity of said antiviral compound that is sufficient to abolish the infectivity of the Human Immunodeficiency Virus present in a volume of said fluid retained in said container.

9. The article of manufacture of claim 1, wherein said container means is a test-tube.

10. The article of manufacture of claim 9, wherein said effective amount is a quantity of said antiviral compound that is sufficient to abolish the infectivity of the Human Immunodeficiency Virus present in a volume of said fluid retained in said container.

11. The article of claim 1 wherein said virus is a member selected from the group consisting of human and domesticated mammalian enveloped viruses.

12. An article of manufacture comprising:
    means for retaining a biological fluid; and
    an antiviral effective amount for inactivating said virus of at least one antiviral effective compound selected from the group consisting of aromatic polycyclic diones; antiviral effective analogs, isomers, homologs and derivatives of said aromatic polycyclic diones; physiologically acceptable salts of said diones, analogs, isomers, homologs and derivatives; and mixtures of said diones, analogs, isomers, homologs, derivatives and salts, and compound being present in said means to contact said fluid when said fluid is introduced into said retaining means.

13. An article in accordance with claim 12, wherein said antiviral compound is selected from the group consisting of hypericin; antiviral effective analogs, isomers, homologs and derivatives of said hypericin; physiologically acceptable salts of said hypericin, analogs, isomers, homologs and derivatives; and mixtures of said hypericin, analogs, isomers, homologs, derivatives and salts.

14. An article in accordance with claim 13, wherein said antiviral compound is hypericin or a physiologically acceptable salt thereof.

15. An article of manufacture in accordance with claim 12, wherein said effective amount is a quantity which is not substantially larger than the minimum amount of said antiviral compound that is effective to terminate any infectivity of the target virus present in a volume of the biological fluid retained in said retaining means.

16. An article of manufacture in accordance with claim 12, wherein said retaining means is other than laboratory glassware.

17. An article of manufacture for contacting a biological fluid and including means to inactivate any virus in such fluid, comprising:
   surface means for contacting a biological fluid which may be contaminated with a virus, and
   an effective amount for inactivating said virus of at least one antiviral compound selected from the group consisting of antiviral effective polycyclic aromatic diones; antiviral effective analogs, isomers, homologs and derivatives of said diones; physiologically acceptable salts of said diones, analogs, isomers, homologs and derivatives; and mixtures of said diones, analogs, isomers, homologs, derivatives and salts, said compound being present on or in said article of manufacture to contact said fluid no later than when said fluid contacts said surface means.

18. An article in accordance with claim 17, wherein said antiviral compound is selected from the group consisting of hypericin; antiviral effective analogs, isomers, homologs and derivatives of said hypericin; physiologically acceptable salts of said hypericin, analogs, isomers, homologs and derivatives; and mixtures of said hypericin, analogs, isomers, homologs, derivatives and salts.

19. An article in accordance with claim 18, wherein said antiviral compound is hypericin or a physiologically acceptable salt thereof.

20. An article of manufacture in accordance with claim 17, wherein said effective amount is a quantity which is not substantially larger than the minimum amount of said antiviral compound that is effective to terminate any infectivity of the target virus present in a volume of the biological fluid which comes into contact with said surface means.

21. An article of manufacture in accordance with claim 17, wherein said surface means is other than the surface of laboratory glassware.

22. In an article of manufacture having surface means for coming into contact with a biological fluid which is infected with a retrovirus, the improvement whereby the infectivity of any retrovirus which comes into contact with said surface means is significantly reduced or completely eliminated, wherein the article of manufacture further includes, in contact with surface means, an effective amount of at least one antiretroviral compound selected from the group consisting of antiviral effective polycyclic diones; antiretroviral effective analogs, isomers, homologs and derivatives of said diones; physiologically acceptable salts of said diones, analogs, isomers, homologs and derivatives; and mixtures of said diones, analogs, homologs, derivatives and salts.

23. An article in accordance with claim 22, wherein said articles is a container and said surface means is the interior surface of the container, and said antiretroviral compound is in contact with said surface means by virtue of being present within said container.

24. An article of manufacture in accordance with claim 22, wherein said effective amount is a quantity which is not substantially larger than the minimum amount of said antiviral compound that is effective to terminate any infectivity of the target virus present in a volume of the biological fluid which comes into contact with said surface means.

25. An article of manufacture in accordance with claim 22, wherein said surface means is other than the surface of laboratory glassware.

26. A method for inactivating any virus present in a biological fluid, comprising:
   placing into a container intended to hold the biological fluid, an effective amount for inactivating any virus which may be present in the fluid, of at least one antiviral compound selected from the group consisting of antiviral effective aromatic polycyclic diones; antiviral effective analogs, isomers, homologs and derivatives of said aromatic polycyclic diones; physiologically acceptable salts of said diones, analogs, isomers, homologs and derivatives; and mixtures of said diones, analogs, isomers, homologs and derivatives and salts; and
   putting the biological fluid into the container.

27. A method in accordance with claim 26 wherein said antiviral compound is selected from the group consisting of hypericin, antiviral effective analogs, isomers, homologs and derivatives of said hypericin; physiologically acceptable salts of said hypericin, analogs, isomers, homologs and derivatives; and mixtures of said hypericin, analogs, isomers, homologs, derivatives and salts.

28. A method in accordance with claim 26, wherein said antiviral compound is hypericin or a physiologically acceptable salt thereof.

29. A method for significantly reducing the infectivity of any virus which is in a biological fluid, comprising:
   placing in contact with a surface of an article of manufacture intended to come into contact with a biological fluid which may be infected with a virus, an effective amount for significantly reducing the infectivity of any virus which is in the biological fluid of at least one antiviral compound selected from the group consisting of antiviral effective aromatic polycyclic diones; antiviral effective analogs, isomers, homologs and derivatives of said aromatic polycyclic diones; physiologically acceptable salts of said diones, analogs, isomers, homologs and derivatives; and mixtures of said diones, analogs, isomers, homologs, derivatives and salts; and
   contacting the biological fluid with said surface.

30. A method in accordance with claim 29 wherein said antiviral compound is selected from the group consisting of hypericin; antiviral effective analogs, isomers, homologs and derivatives of said hypericin; physiologically acceptable salts of said hypericin, analogs, isomers, homologs and derivatives; and mixtures of said hypericin, analogs, isomers, homologs, derivatives and salts.

31. A method in accordance with claim 29, wherein said antiviral compound is hypericin or a physiologically acceptable salt thereof.

* * * * *